(12) United States Patent
Besemer et al.

(10) Patent No.: US 6,331,619 B1
(45) Date of Patent: Dec. 18, 2001

(54) SUPERABSORBENT MATERIAL AND METHOD FOR PRODUCING SAID MATERIAL

(75) Inventors: Arie Cornelis Besemer, Amerongen; Jeffrey Wilson Thornton, Hulzen, both of (NL)

(73) Assignee: SCA Hygiene Products Zeist B.V., Zeist (NL)

( * ) Notice: Subject to any disclaimer, the term of this patent is extended or adjusted under 35 U.S.C. 154(b) by 0 days.

(21) Appl. No.: 09/331,259

(22) PCT Filed: Dec. 18, 1997

(86) PCT No.: PCT/NL97/00708

§ 371 Date: Jul. 27, 1999

§ 102(e) Date: Jul. 27, 1999

(87) PCT Pub. No.: WO98/27117

PCT Pub. Date: Jun. 25, 1998

(30) Foreign Application Priority Data

Dec. 18, 1996 (EP) .................................................. 96203594
Dec. 18, 1996 (EP) .................................................. 96203595

(51) Int. Cl.[7] .................................................. C08B 31/18
(52) U.S. Cl. ........................... 536/105; 536/56; 536/106; 536/114; 536/119; 536/123.1; 536/124
(58) Field of Search ................................ 536/123.1, 124, 536/56, 105, 114, 119, 106

(56) References Cited

U.S. PATENT DOCUMENTS

| | | |
|---|---|---|
| 2,929,811 | 3/1960 | Hofreiter et al. . |
| 2,989,521 | 6/1961 | Senti et al. . |
| 5,346,892 | 9/1994 | Fitt et al. . |

FOREIGN PATENT DOCUMENTS 0023561  2/1981  (EP) .

OTHER PUBLICATIONS

"Paper strengthening agent", Chemical Abstracts, vol. 97, No. 6, Aug. 9, 1982, Columbus, Ohio, US; Abstract No. 40606.

*Primary Examiner*—Elli Peselev
(74) *Attorney, Agent, or Firm*—Young & Thompson

(57) ABSTRACT

A superabsorbent polysaccharide derivative is obtained by oxidation of the polysaccharide to the extent that the derivative contains 0.2–0.3 carboxyl group per monosaccharide unit and cross-linking the oxidized polysaccharide with 0.0001–0.2 equivalent of cross-linking agent per monosaccharide unit. The polysaccharide may also be cross-linked prior to oxidation.

17 Claims, No Drawings

SUPERABSORBENT MATERIAL AND METHOD FOR PRODUCING SAID MATERIAL

This application is a 371 of PCT/NL97/00708 filed Dec. 18, 1997.

The present invention relates to a superabsorbent material based on polysaccharides and to a method of producing such material. A superabsorbent material is defined as a material capable of absorbing at least 20 times its own weight of water.

Superabsorbent materials of various types are known in the art. Examples are crosslinked polyacrylates and polysaccharides and with polyacryltes. A problem related to the use of superabsorbent materials is that such materials are normally based on non-renewable and/or non-biodegradable raw materials. Consequently, there is a need for superabsorbent materials which are wholly based on renewable raw materials, such as polysaccharides, and are degraded by microorganisms or other natural agents after being disposed of.

EP-A-489424 discloses modified starch compositions useful as absorbable dusting powders, obtained by slight hypochlorite oxidation of starch resulting in the presence of 0.05–0.5 wt. % of carboxyl groups (=0.002–0.018 carboxyl groups per monosaccharide unit), followed by partial crosslinking with 0.05–1.1 wt. % of phosphorous oxychloride. The powders obtained according to this prior art are not suitable for use in absorbent articles such a diapers, sanitary napkins and the like due to the fact that they do not swell to a significant extent. Kulicke et al (Starch/Stärke, 41 (1989) 140–146; ibid. 42 (1990) 134–141) have studied the effect of crosslinking with epichlorohydrin and sodium trimetaphosphate, respectively, on the absorption capacity of starch, amylopectin and commercial oxidised starch, which contains carbonyl (aldehyde or ketone) groups and carboxylic acid groups. The degree of oxidation of such oxidised starch is presumably lower than 10%. The purpose of obtaining oxidised starch was to obtain thin boiling starch (lower molecular weight). According to these authors, the absorption capacity decreases with increased crosslinker concentration and the absorption capacity of crosslinked oxidised starch is higher than that of crosslinked native starch. Although a considerable swelling capacity in pure water was reported, the swelling capacity of the crosslinked polymers in water containing sodium chloride or other salt drops to about 15 g per g polymer. U.S. Pat. No. 2,929,811 discloses crosslinking (using epichlorohydrin) and subsequent slight oxidation (<5 mol %), using periodate and chlorite, of starch for improving the viscosity characteristics of the starch. No water-absorbing properties are reported.

EP-A-23561 discloses a water-absorbing crosslinked polycarboxycellulose which is produced by carboxymethylation of cellulose, crosslinking by acid-catalysed internal esterification, and slight oxidation (<5 mol %) using periodate/bromine, lead tetraacetate or hydrogen peroxide. A disadvantage of carboxymethyl celluloses is that they are relatively expensive.

It has now been found that a superabsorbent material having an absorption capacity of at least 20 times its own weight, and based on natural, biodegradable polysaccharides, can be obtained by introducing at least 0.2 carboxyl groups per mono-saccharide unit, at least 0.1 of which is formed by oxidising a carboxyl group of the polysaccharide, and subsequently slightly crosslinking the oxydised polysaccharide.

The polysaccharides to be used according to the present invention are in particular α-glucans like starch, amylose and amylopectin, β-glucans like cellulose, galactomannans like guar gum (guaran) and locust bean gum, glucomannans including e.g. xanthan gum, fructans, (arabino)xylans, galactans including alginates and pectins, as well as non-ionic derivatives such as hydroxyethyl and hydroxypropyl derivatives of such polysaccharides. Starch and guar, and to a somewhat lesser extent, cellulose, are preferred for economic reasons. The chain of the polysaccharides is important although there is no critical minimum for the molecular weight. In general, polysaccharides having a molecular weight of more than 1,000 are preferred. A molecular weight above about 25,000 may have a positive effect on the properties of the oxidised product.

The polysaccharides to be used according to the present invention may also be carboxymethylated or carboxyethylated, especially in the case of α-glucans like starch, galactomannans and glucomannans. Other carboxyalkylated polysaccharides include the half esters obtained from cyclic anhydrides such as succinic and maleic anhydride (groups having the formula —O—CO—$CH_2$—$CH_2$—COOH or —O—CO—CH=CH—COOH), and addition products of maleic half esters to which sulphite has been added (groups having the formula —O—CO—$CH_2$—CH($SO_3H$)—COOH). The degree of carboxyalkylation is preferably between 0 and 1.5, in particular between 0.1 and 1.0 carboxyalkyl groups per monosaccharide unit. Carboxymethylation and carboxyethylation can be performed in a conventional manner, i.e. by reaction of the (oxidised or non-oxidised polysaccharide with monochloroacetate, or acrylonitrile followed by hydrolysis, respectively, or by hydroxyethylation (or hydroxypropylation) followed by oxidation of the primary hydroxy groups, e.g. using a nitroxyl catalyst as described below. Thus, a useful type of products according to the invention containing both 6-carboxyl groups and carboxymethyl groups can be obtained in several ways: oxidation of carboxymethylated polysaccharide, carboxymethylation of 6-oxidised polysaccharide, (primary hydroxyl) oxidation of hydroxyethylated polysaccharide, and hydroxyethylation and oxidation of 6-oxidised polysaccharide.

The oxidation of the polysaccharide is an essential step of the present invention. The oxidation should be performed to a substantial degree, i.e. until at least 0.1 of the carbinol group per monosaccharide unit has been oxidised to a carboxyl group. The term carbinol group covers both primary, exocyclic hydroxymethyl groups (—$CH_2OH$) and secondary, usually endocyclic hydroxymethylene groups (—CHOH—) of the polysaccharide Preferably at least 0.15 or even at least 0.2 carbinol group have been oxidised to a carboxyl group per monosaccharide unit. Additional carboxyl groups may be present in the form of carboxymethyl groups introduced by substitution on a hydroxyl group.

Oxidation of polysaccharides is well documented. Oxidaton can be performed using various oxidising agents, which result in various degrees of oxidation, various degrees of polymerisation and different sites of oxidation. Oxidation of polysaccharides can be focused at primary hydroxyl group, like the 6-hydroxyl group in the anhydroglucose units of glucans, which results in carboxyl-polysaccharides with preserved ring structures. On the other hand, the oxidation can be mainly directed at a vicinal diol function present in the monosaccharide rings, such as the C2-C3 site in anhydroglucose units This results in cleavage of the monosaccharide units with the production of dialdehyde and/or dicarboxyl functions.

As an example, the oxidation of starch with nitrite and nitrate in phosphoric acid, mainly resulting in 6-carboxy starch, is described in NL patent application 9301172. An improved oxidation of the 6-hydroxyl groups in starch, using a hypohalite in the presence of a di-tert-alkynitroxyl catalyst is disclosed in WO 95/07303. Examples of oxidation of glucans at the C2-C3 function include the process according to EP-A427349, using low levels of hypobromite, and the process according to WO 94/21690, which uses hydrogen peroxide in the presence of alkali metal; or transition metals. WO 95/12619 describes an improved oxidation of starch with periodic acid, resulting in dialdehyde starch with extensive regeneration of a periodic acid. The dialdehyde starch can be further oxidised to dicarboxyl starch using e.g sodium chlorite and/or hydrogen peroxide. Also, dialdehyde starch can be further oxidised with iodine or bromine or with nitrogen dioxide producing dicarboxy or up to tricarboxy starch. Other known oxidation methods include metal-catalysed oxidation, eg, using ruthenium, anhydrous oxidation using nitrogen dioxide in e.g. halocarbons and enzymatic and chemo-enzymatic oxidation of starch, guar and other polysaccharides, and these can also be used in the present invention. In case of galactomannans, which have terminal galactose units, enzymatic oxidation using galactose oxidase (EC 1.1.3.9) can also be used to introduce aldehyde groups, which can easily be converted to carboxyl groups, e.g. using hypoiodite.

Any of the known oxidation processes can be used according to the present invention. Also, a combination of oxidation processes and/or oxidation agents can be used. Oxidation of primary hydroxyl functions in the polysaccharides has a slight advantage, in that the resulting carboxyl functions on average at a wider distance than the carboxyl groups Introduced by C2-C3 oxidation and therefore allow a somewhat lower average degree of oxidation. The oxidation of starch and other polysaccharides using hypochlorite in the presence of di-tert-alkylnitroxyl catalysts, in particular tetramethylpipdine-N-oxyl (TEMPO) is particularly efficient.

The degree of oxidation is such that more than 1.0 out of each 10 monosaccharide units is oxidised to produce a carboxy- or dicarboxy-monosaccharide unit. The number of dicarboxy-monosaccharide units may be up to 10 out of 10, but is preferably between 2 and 8 out of 10, and most preferably between 2 and 6. Expressing the degree of oxidation in a carboxyl content, the polysaccharide contains on average 0.2–3.0 carboxyl group per monosaccharide unit, preferably 0.4–1.6 and most preferably 0.4–1.2 carboxyl group per monosaccharide unit. The total carboxyl content (both resulting from carboxy-alkylation and from oxidation) in case of carboxyalkylated polysaccharides is preferably between 0.2 and 2 carboxyl groups per C-6/7 unit.

Dicarboxy-monosaccharide units especially result from C2-C3 oxidation such as hypohalite oxidation. The dicarboxy-monosaccharide units are usually ring-opened units having a higher charge distribution and more water-binding capacity. On the other hand C2-C3 oxidation leads to more extensive degradation (depolymerisation) of the polysacchride unless more expensive oxidising agents such as periodate are used. Mono-carboxy-monosaccharide units especially result from C6 oxidation such as TEMPO oxidation. Such oxidations are usually less accompanied by degradation.

The oxidised polysaccharide is subsequently reacted with a crosslinking agent. Crosslinking agents are reagents containing two or more functions capable of reacting with a hydroxyl group, resulting in intra- and inter-molecular bonds between different mono-saccharide units. Suitable crosslinking agents may act on the hydroxyl groups of different polysaccharide chains and include divinyl sulphone, epichlorohydrin, diepoxybutane, diglycidyl ethers, diisocyanates, cyanuric chloride, trimetaphosphates, phosphoryl chloride, and mixed anhydrides, and also inorganic crosslinkers such as aluminiun and zirconium ions, but are not restricted to these examples. Crosslinking can also be performed using carboxyl or aldehyde groups formed by oxidation or carboxyl groups introduced by carboxyalkylation, e.g. using polyols, polyamines or other polyfunctional reagents. Esterification and other crosslinking methods described herein can also be effected intramolecularly at the surface between the carboxyl group of one polysaccharide chain and a hydroxyl group of another chain as known in the art. This inter-chain crosslinking can be catalysed by an acid or a multivalent ion such as magnesium or calcium, or by description of crosslinking agents and reaction conditions can be found e.g. in "*Starch Derivatives: Production and Uses*" by M. W. Rutenberg and D. Solarek, Acad. Press Inc., 1984, pages 324–332.

The crosslinking after oxidation to the desired level of crosslinking can be achieved by reacting the oxidised polysaccharide with 0.1–20 mol. % of crosslinking agent, preferably 0.2–10 mol. % and most preferably 0.3–2 mol %. Optimum crosslinking rates and conditions depend an the particular polysaccharide and on the particular crosslinking agent, as well as on the type of oxidation: for C6 oxidation, the optimum rate may be e.g. 0.3–0.5 mol %, while for C2-C3 oxidation the optimum may be somewhat higher, e.g. 0.5–2 mol %. Reagents such as diglycidyl ether are usually reacted under acidic conditions, whereas most other reagents are reacted under neutral or alkaline conditions. Reaction conditions and working-up procedures are described e.g in U.S. Pat. No. 4,582,865. Work-up may be done by drawing off the aqueous solution of crosslinking agent of the crosslinked or gelatinised polysaccharide, drying the latter under air, under reduced pressure and/or in a drying oven, optionally using water-miscible and/or volatile solvents such as methanol, ethanol, isopropanol, acetone, dioxane or tetrhydrofuran, flowed e.g. by freeze-drying spray-drying, vacuum-drying or other appropriate technique. Crosslinking preferably results in a gel, that may precipitate from the reaction medium.

It is sometimes advantageous to perform a crosslinking before the oxidation reaction. This crosslinking can be performed using the same agents and the same conditions as the post-linking described above. In general, the level of prior crosslinking is lower than that of the post-crosslinking. For example, the prior crosslinking can be performed using 0.05–1.0 preferably 0.1–0.8, most preferably 0.1–0.5 mol. % of crosslinking agent, such as epichlorohydrin. It is preferred that the salt concentration of the polysaccharide solution during crosslinking is low; this results in a better accessibility of the polysaccharide for the crosslinking agents. Some pre-crosslinked starches are commercially available and can be used in the present invention. In some instances, prior crosslinking, without post-crosslinking, may be sufficient, e.g. when oxidation of the polysaccharide is performed at the 6-position such as with TEMPO, or when oxidation is combined with carboxyalkylation.

The superabsorbent polysaccharide according to the invention has improved absorption characteristics, especially of body fluids which contain various salts and non-ionic substances. The product is particularly suitable for the production of absorbent hygiene articles, such as diapers, sanitary napkins and the like. Such articles can be produced entirely on the basis of the polysaccharides according to the invention, but they can also contain conventional absorbent materials, such as cellulose pulp in addition to the absorbents according to the invention.

EXAMPLE 1

Preparation of 2,3-dicarboxy starch

In a cooled dispersion of non-crosslinked potato starch (16.2 grams of dry substance) in 300 ml water sodium periodate was added at 5° C. (7 g 9.6 g, and 12.8 g to obtain a degree of oxidation of 35, 45 and 60%, respectively) The pH was adjusted to 5 and the mixture was stirred in the dark for 20 hours at 5° C. Unreacted sodium iodate was then removed by filtration and repeated washings with water. The dialdehyde starch thus obtained (15.6 g) was suspended in chilled water (100 ml) and the pH was adjusted to 5. Stoichiometric amounts of sodium chlorite and hydrogen peroxide were added, i.e. 2 moles of $NaClO_2$ (8.0, 10.2 and 13.6 g, respectively) and 2 moles of $H_2O_2$ (7.3, 9.3 and 12.4 g, respectively) were used per mole of sodium periodate. The mixture was filtered at 5° C., keeping the pH at 5 by addition of NaOH. Addition of water was required to keep the mixture stirred After three hours the pH remained more or less consistent without the need of adding alkali. After 20 hours the reaction mixture was poured into three volumes of ethanol. A gelly precipitate was formed, from which the aqueous solution was decanted. The precipitate was dissolved in water and the procedure was repeated. The second precipitate was a solid and was collected by filtration and dried in vacuo at 50° C. The overall yield was 90%, calculated on the starting starch, and the carboxyl content was 32, 42 and 55 9, respectively.

EXAMPLE 2

Preparation of pre-crosslinked 2,3-dicarboxy starch

The procedure of example 1 was repeated, starting with epichlorohydrin-crosslinked starch instead of native starch. The overall yield and the carboxyl content were the same.

EXAMPLE 3

Crosslinking of 2,3-dicarboxy starch

An amount of 15, 20 as 30 wt. % of 45% oxidised starch (dicarboxy starch, example 1) was dissolved in 100 ml of 0.1 M aqueous NaOH for 4 hours. At room temperature an amount of 2, 5 or 8 mole % of divinyl sulphone (0.5 mole % being 1.8/200 g DVS per g of dicarboxy starch) was added to the solution and mixed. The reaction mixture was left overnight at room temperature. The resulting gel was then washed with distilled water and subsequently with acetone and then dried at room temperature. The absorption capacity of the resulting crosslinked oxidised starch was measured for pure water and for synthetic urine. The composition of the synthetic urine (SU) is as follows:

300 mM of urea
60 mM of KCl
130 mM of NaCl
3.5 mM of $MgSO_4$
2.0 mM of $CaSO_4.2H_2O$
1 g/l of a 0.1% solution of Triton X-100 (Riedel de Haen); in deionised water.

The results are given in table 1.

EXAMPLE 4

Crosslinking of pre-crosslinked 2,3 dicarboxy starch

The procedure of example 3 was repeated, using pre-crosslinked, oxidised starch according to example 2. The results are given in table 1.

EXAMPLE 5

Crosslinked dicarboxy starch

Following the procedure of example 1 and 3, starch was oxidised with periodate and chlorite to an oxidation degree of 50% and subsequently crosslinked as a 30 wt. % solution with 2 mol % divinyl sulphone. The product was isolated by precipitation from methanol and had a free swelling capacity (FSC) in synthetic urine (see example 3) of 42 g/g.

TABLE 1

Water absorption capacities of crosslinked 45% oxidised dicarboxy-starch

| % pre-XL/wt. % sol/ % post-XL | abs.capac. 60 min. | abs. capac. 120 min. | retention capac. |
| --- | --- | --- | --- |
| 0/20/2 | 25.9 | 26.2 | 19.7 |
| 0/30/2 | 22.9 | 20.8 | 15.7 |
| 0/20/5 | 25.0 | 24.8 | 18.7 |
| 0/15/8 | 24.2 | 22.9 | 17.4 |
| 0/20/8 | 21.5 | 22.1 | 14.5 |
| 0.5/30/2 | 29.1 | 28.9 | 16.7 |
| 0.5/20/5 | 24.4 | 25.6 | 16.2 |
| 0.5/30/5 | 21.6 | 20.4 | 14.4 |
| 0.5/15/8 | 26.4 | 25.9 | 15.3 |
| 0.5/20/8 | 24.4 | 24.2 | 17.4 |

% pre-XL   mole percentage of epichlorohydrin used for pre-crosslinking with respect to anhydroglucose units
wt. % sol.   weight percentage of oxidised starch before post-crosslinking
% post-XL   mole percentage of divinyl sulphone used for post-crosslinking with respect to anhydroglucose units

EXAMPLE 6

Preparation of 6-carboxy starch

A dispersion of 16.2 g (dry matter) of noncrosslinked potato starch (100 mmol of monosaccharide units) in 300 ml of water was prepared. 45 mg of TEMPO and 450 mg of sodium bromide were dissolved in the gelatinised mixture. A solution of sodium hypochlorite, 3.5 meq of hypochlorite per ml, was added (90, 146 and 192 ml in three experiments to obtain a degree of oxidation of 40, 60 and 80%, respectively). The pH of the mixture was kept at 10 throughout the process by adding sodium hydroxide solution using a pH stat. After a fast reaction, the reaction ceased within 30 minutes, indicated by the fact that no further sodium hydroxide addition occurred. The degree of oxidation was determined from the consumption of hydroxide. After 1 hour, 100 mg of sodium boro-hydride was added to remove free aldehyde groups. The product was isolated by pouring the reaction mixture into ethanol as described in example 1. The yield was 90%, and the carboxyl content corresponded to the degree of oxidation.

EXAMPLE 7

Crosslinking of 6-carboxy starch

6-Carboxy starch (degree of oxidation 40% or 60%, example 6) was dissolved in water (concentration 20%) at pH 11–12 and cooled to 0–2° C. A 10% solution of divinyl sulphone was added (2 or 3 mole %=8 or 12 mg, respectively) and after homogenisation the mixture was allowed to stand for 4 hours. The temperature was allowed to rise to 20° C. The crosslinked polymer was isolated by pouring the mixture in ethanol (1 volume of reaction to 3 volumes of ethanol), The precipitate was collected by filtration, washed twice with absolute ethanol and dried In vacuo. The water binding capacity a 15 minutes using synthetic urine was determined to be:

| 40% oxidation | 2 mole% of water | 23 g/g |
| 40% oxidation | 3 mole% of water | 23 g/g |
| 60% oxidation | 2 mole% of water | 21 g/g |
| 60% oxidation | 3 mole% of water | 21 g/g |

After 2 hours, the water binding capacity rises with another 10–15 g/g.

EXAMPLE 8

Crosslinked 6-carboxy starch

Following the procedure of examples 6 and 7, s was oxidised at the 6-position using an amount of oxidising agent to obtain a degree of oxidation of 60%, and was subsequently crosslinked with divinyl sulphone in an amount of 0.5mol %. After work-up the product had an FSC (free swelling capacity) in synthetic urine (see example 3) after 2 hours of 53 g/g, The FSC in 0.9% NaCl was 62 g/g. When the procedure was repeated started with starch which was pre-crosslinked with 0.05 wt. % epichlorohydrin, an FSC in synthetic urine of 49 g/g was obtained.

EXAMPLE 9

Pre-crosslinking and 6-oxidation of starch

Potato starch (5.0 g) was dissolved in 0.5 mol sodium hydroxide. Then 2.5 g of sodium trimetaphosphate (26 mol % with respect to starch) was added. After mixing thoroughly, the samples were kept at 40° C. for 2 hours and then at room temperature for 16 hours. The gels which were obtained were broken into small particles using a mechanical stirrer. The particles were washed with oxidised water until the pH was below 9. The crosslinked starch was then oxidised with TEMPO and hypochlorite/bromide (see example 6), using an amount of hypochlorite corresponding to a degree of oxidation of 60%. The product was then precipitated with ethanol, washed with acetone and dried in a vacuum oven. The FSC value after 1 hour in synthetic urine was 26.7 g/g.

TABLE 2

FSC and CRC (centrifuge retention capacity) values of post-crosslinked oxidised carboxymethyl starch; values corrected for water still present in sample

| % oxidation | mol% DVS | FSC (g/g) SU/2h | FSCC (g/g) 0.9% NaCl/2h | CRC (g/g) SU |
|---|---|---|---|---|
| 17.5 | 0.1 | 22.4 | 31.5 | 1.6 |
| 17.5 | 0.2 | 49.6 | 77.8 | 10.2 |
| 17.5 | 0.3 | 76.6 | 87.9 | 23.5 |
| 17.5 | 0.5 | 61.2 | 80.2 | 17.6 |
| 17.5 | 0.5 | 61.2 | 79.9 | 16.7 |
| 35 | 0.2 | 64.9 | — | 21.2 |
| 35 | 0.4 | 55.2 | — | 35.2 |
| 35 | 0.6 | 44.9 | — | 30.8 |
| 40 | 0.2 | 61.1 | — | 23.2 |
| 40 | 0.4 | 42.8 | — | 30.6 |
| 40 | 0.6 | 30.8 | — | 20.4 |

EXAMPLE 10

6-Oxidation and crosslinking of carboxymethyl starch

Carboxymethyl starch, 10 g (degree of substitution 0.5) was dissolved in 800 ml of demineralised water. 40 mg of TEMPO and 1 g of NaBr were added. An amount of hypochlorite was added corresponding to a degree of oxidation of 17.5%. The hypochlorite was added in portions of 2.5 ml at a time. The pH was kept at 9.5 using 0.5 mol/l sodium hydroxide. After the oxidation reaction was complete, residual aldehyde groups removed by adding 0.5 g of sodium borohydride and for 1 hour. The product was then precipitated using 4 times the volume of ethanol, washed with acetone and dried in a vacuum oven. After drying, the product (1 g) was crosslinked with divinyl sulphone (DVS). Different amounts of DVS were used in mol % with respect to the starch, 0.05, 0.1, 0.2, 0.3, 0.4 or 0.5 mol % was used. The required amount of DVS was added as a 0.1% solution to the samples which were dissolved in 4 ml 0.5 mol/l sodium hydroxide at 5° C. The mixtures were vortexed strongly and placed overnight at 5° C. The next day the gels were broken with a mechanical stirrer. Then 3 ml of 0.2 mol/l acetic acid and 17 ml of demineralised water was added. The gels were left swelling for 1 hour and then precipitated with ethanol, washed with acetone and dried in a vacuum oven. After the samples were dried, the FSC values were determined in synthetic urine (see example 3) or in 0.9% NaCl after 2 hours. The results are given in table 2. The procedure of this example was repeated using an amount of hypochlorite equivalent to 35% and 40% of oxidation instead of 17.5%, The results are also given in table 2.

EXAMPLE 11

Oxidation and crosslinking of guar

Purified guar gum, (1 g, 6.2 mol/l monosaccharide units) was dissolved in 400 ml water and the solution was heated and stirred overnight. After cooling to 5° C. 10 mg TEMPO and 100 mg NaBr were added. Oxidation was started by adding 3.0 ml of NaOCl solution in small steps. The pH was kept between 9.0 and 9.5 with 0.5 NAOH. After the reaction was completed $NaBH_4$ was added andafe 15 min. the pH of the solution was adjusted to 6.5 with 4 M HCl. The oxidised guar product isolated by precipitating in 3 l of a 80/20 (v/v) mixture of ethanol/water and washing the precipitate with 1 l of ethanol (96%). The carboxyl content was determined the method of Blumenkrantz (N. Blumenkrantz and and G. Asboe-Hansen, *Anal. Biochem.* 54 (1973) 484–489); the oxidation degree was 35%. The oxidised material was crosslinked with 3 mol of divinyl sulphone and a weak gel was obtained. The crosslinked product was isolated by precipitating the weak gel in ethanol. The precipitate was dried in a vacuum oven. The free swelling capacity (FSC) of the isolated product in 2 hours and the centrifugal retention capacity (CRC) were determined in synthetic urine (see example 3) The FSC was 40 g/g and th CRC was 25 g/g.

What is claimed is:

1. Superabsorbent polysaccharide derivative obtained by oxidation and crosslinking of a polysaccharide selected from the group consisting of starch, amylose and amylopectin, β-glucans, galactomannans, glucomannans and fructans, hydroxyethyl and hydroxypropyl derivatives thereof, and carboxyalkyl derivatives of starch, amylose, amylopectin, galactomannans and glucomannans, characterized in that at least 0.1 carbinol group per monosaccharide unit of the polysaccharide derivative has been oxidized to a carboxyl group, the total number of carboxyl groups per monosaccharide unit being 0.2–3.0, and the derivative results from reaction with 0.001–0.2 equivalent of crosslinking agent per monosaccharide unit.

2. Superabsorbent polysaccharide denrivative according to claim 1, containing 0.4–1.6 carboxyl group per monosaccharide unit, at least 0.2 of which is formed by oxidation of a carbinol group.

3. Superabsorbent polysaccharide derivative according to claim 1, wherein said polysaccharide derivative is an α-glucan, galactomannan or glucomannan.

4. Superabsorbent polysaccharide derivative according to claim 3, wherein 0.1–1 carboxyl groups per monosaccharide unit are present as carboxyalkyl groups.

5. Process of producing a superabsorbent polysaccharide derivative by oxidation and crosslinking a polysaccharide, characterised in that the polysaccharide is oxidised to obtain a polysaccharide containing an average of at least 0.2 carboxyl groups per monosaccharide unit and is subsequently reacted with 0.001–0.2 equivalent of a crosslinking agent.

6. Process according to claim 5, wherein the polysaccharide is oxidised using hypochlorite, optionally in the presence of a di-tert-alkylnitroxide.

7. Process according to claim 5, wherein the polysaccharide is oxidised using periodate, optionally followed by chlorite oxidation.

8. Process according to claim 5, wherein the oxidised polysaccharide is reacted with 0.002–0.1, preferably 0.005–0.05 equivalents of crosslinking agent per monosaccharide unit.

9. Process according to claim 5, wherein, before the oxidation, the polysaccharide is reacted with a crosslinking agent.

10. Process according to claim 5, wherein, before or after the oxidation, the polysaccharide is carboxyalkylated to a degree of substitution of 0.1–1 carboxyalkyl groups per monosaccharide unit.

11. Process of producing a superabsorbent polysaccharide derivative by oxidation and crosslinking a polysaccharide, characterised in that the polysaccharide is crosslinked by reaction with a crosslinking agent and subsequently oxidised using hypochlorite in the presence of a di-tert-alkylnitroxide to a degree corresponding to an average of at least 0.2 carboxyl groups per monosaccharide unit.

12. Process according to claim 5, wherein the crosslinking agent is selected from the group consisting of epichlorohydrin, a trimetaphosphate, phosphoryl chloride, divinyl sulphone, diglycidyl ether, a diisocyanate, and a mixed anhydride.

13. Process according to claim 5, wherein the polysaccharide is an α-glucan, galactomannan or glucomannan.

14. Process according to claim 11, wherein the crosslinking agent is selected from the group consisting of epichlorohydrin, a trimetaphosphate, phosphoryl chloride, divinyl sulphone, diglycidyl ether, a diisocyanate, and a mixed anhydride.

15. Process according to claim 11, wherein the polysaccharide is an α-glucan, galactomannan or glucomannan.

16. Process of producing a superabsorbent polysaccharide derivation by oxidation and crosslinking a polysaccharide, characterized in that the polysaccharide is an α-glucan, galactomannan or glucomannan which is carboxyalkylated to a degree of 0.1–1 carboxyalkyl groups per monosaccharide unit and oxidized to a degree corresponding to at least 0.1 carboxyl groups per monosaccharide unit, the total average number of carboxyl group per monosaccharide unit being at least 0.2, and which is pre- and/or post-crosslinked by reaction with a crosslinking agent or by interchain esterification;

wherein the crosslinking agent is selected from the group consisting of epichlorohydrin, a trimetaphosphate, phosphoryl chloride, divinyl sulphone, diglycidyl ether, a diisocyanate, and a mixed anhydride.

17. Superabsorbent polysaccharide derivative according to claim 3, wherein said polysaccharide derivative is starch or guar or a starch or guar derivative.

* * * * *